United States Patent
Jablonka et al.

(10) Patent No.: US 7,361,154 B2
(45) Date of Patent: Apr. 22, 2008

(54) STRAP FOR TREATING MEDICAL AILMENTS

(75) Inventors: James M. Jablonka, 108 Longvue Dr., Wethersfield, CT (US) 06109; Vera Killian, Andover, CT (US)

(73) Assignee: James M. Jablonka, Wethersfield, CT (US)

( * ) Notice: Subject to any disclaimer, the term of this patent is extended or adjusted under 35 U.S.C. 154(b) by 0 days.

(21) Appl. No.: 10/935,829

(22) Filed: Sep. 8, 2004

(65) Prior Publication Data

US 2006/0052735 A1    Mar. 9, 2006

(51) Int. Cl.
*A61F 13/00* (2006.01)
(52) U.S. Cl. .......................... 602/20; 602/62
(58) Field of Classification Search ................. 602/20, 602/26, 23, 206, 60, 61, 62, 75, 53
See application file for complete search history.

(56) References Cited

U.S. PATENT DOCUMENTS

| | | | | |
|---|---|---|---|---|
| 5,295,951 A | * | 3/1994 | Fareed ........................ | 602/62 |
| 5,921,949 A | * | 7/1999 | Dray ........................... | 602/64 |
| 6,149,616 A | * | 11/2000 | Szlema et al. ................ | 602/62 |
| 6,398,749 B1 | * | 6/2002 | Slautterback ................ | 602/62 |
| 6,755,800 B2 | * | 6/2004 | Weaver et al. ................ | 602/62 |

* cited by examiner

*Primary Examiner*—Kim M Lewis
(74) *Attorney, Agent, or Firm*—Lerner, David, Littenberg, Krumholz & Mentlik, LLP

(57) ABSTRACT

A therapeutic pressure strap having an elongated flexible band. The band includes a first end and a second end, an interior surface, and an exterior surface. The interior surface of the band is adapted for contacting a human limb having a tendon. The stage may include a fastener attached to the band capable of securing the band in a closed loop. At least two pads are disposed on the interior surface of the band in a spaced apart relationship. The pads are adapted to be positioned against the human limb on adjacent sides of the tendon.

11 Claims, 9 Drawing Sheets

STRAP FOR TREATING MEDICAL AILMENTS

BACKGROUND OF THE INVENTION

The present invention relates in general to flexible straps which are easy to apply, comfortable to wear and are useful for alleviating discomfort associated with tendons, specifically those arising from the medial and lateral epicondyle and patellar tendon.

Support bands are currently produced in a variety of designs. Generally, a support band is designed to supply compression to the forearm or knee joint to alleviate symptoms associated with lateral epicondylitis, medical epicondylitis, patellar tendinitis or the like.

Patellar tendinitis is the inflammation of the patellar tendon at the point at which it attaches to either the inferior pole of the patella or the tibial tuberosity. Patellar tendinitis may also be caused by inflammation of the body of the tendon, quadriceps tendon at the point at which it attaches to the superior pole of the patella. Patellar tendinitis is primarily caused by continuous stress on the patellar or quadriceps tendons. Although repetitive jumping, such as that which occurs while playing soccer or basketball, is an activity commonly associated with aggravating the onset of patellar tendinitis, there are several other activities that can cause rapid growth of the condition, such as running, walking, bicycling or trauma.

Tennis elbow is the inflammation of a tendon, muscle or tendon sheath located at the lateral epicondyle. Tennis elbow is primarily caused by repetitive stress on the extensor and supinator muscles of the forearm. There are several other activities responsible for this condition such as continuous use of hand tools, turning knobs/handles, trauma, painting with a brush and maintaining static posture for prolonged periods of time. Each of these activities requires repetitive use of the same muscle groups, which may lead to overuse and inflammation and micro-tearing associated with medial and lateral epicondylitis, patellar and various other forms of tendinitis.

Although some severe or chronic cases of tendinitis may require the use of anti-inflammatory drugs or surgical intervention, the vast majority of cases are resolved using simpler methods. Standard treatment for a typical case of tendinitis involves applying ice to and resting the affected area and alleviating any associated pain. In many cases, an external device will also be used to support the affected tissue, thereby reducing the risk of further injury while allowing time for the damaged area to heal.

While prompt diagnosis and treatment of tendinitis can minimize the pain associated with the condition and reduce the extent of treatment needed, prior art methods available for treatment often fail to provide adequate relief. A typical external elbow wrap used to treat lateral epicondyle tennis elbow consists of nothing more than an elastic strap which extends around the forearm with possibly a means to apply force directly to the involved muscles. This type of prior art strap does not provide concentrated support directly over the injured area. Those devices which do attempt to direct support specifically to the injured region generally apply direct pressure against a part of a bone or tendon. In fact, various straps and bands have been configured either by applying circumferential pressure against the affected area or direct pressure against the tendon. Although the straps generally have had limited success in alleviating discomfort associated with tendonitis, a new method and device for treatment is still required.

SUMMARY OF THE INVENTION

The present invention discloses a therapeutic pressure strap. The pressure strap includes an elongated flexible band having a first end, a second end, an interior surface and an exterior surface.

The interior surface of the band is adapted for contacting a human limb having a tendon. The therapeutic pressure strap preferably also includes a fastener attached to the band capable of securing the band in a closed loop. At least two pads are preferably disposed on the interior surface of the band in a spaced-apart relationship. The pads are adapted to be positioned against a human limb on adjacent sides of a tendon.

In one preferred embodiment, the pads are removably disposed on the interior surface of the band. The strap may include hooks or loops, such as Velcro®, disposed on the interior surface of the band and corresponding hoops or loops disposed on the removable pads.

The band is preferably placed about the circumference of a human limb, with the second end being received in the fastener and pulled through the fastener, causing the band to tighten about the limb. As the strap is tightened, the pads apply a lateral force against the tendon. The fastener is adapted for releasably securing the first and second ends together. The band is preferably adapted for applying compressive force to a human limb having a tendon with the pads adapted for applying the compressive force to the tendon when a tendon is received between the pads.

In one embodiment, the first and second ends of the band are joinable to form a closed loop.

The therapeutic strap may further include a means for applying a compressive force to a human limb having a tendon and a means for applying the compressive force to the tendon. The therapeutic strap may further include a means for adjusting the compressive force applied to the tendon. Additionally, the present invention is directed towards a method of treating discomfort associated with a tendon. The method includes applying lateral pressure to the lateral sides of a tendon. The tendon may originate from the medial or lateral epicondyle tendon or, in an alternate embodiment, the tendon may be a patella tendon.

The step of applying lateral pressure may include an elongated strap being placed around the limb and bearing against a tendon. At least two pads are disposed on the strap and the limb so the strap holds the pads against the lateral sides of the tendon. The pad may be positioned against the limb on adjacent sides of the tendon and the band tightened to close the pads to apply lateral pressure to the tendon.

The step of applying lateral pressure may include pinching a portion of the skin overlying the tendon in order that the tendon is drawn within a gap formed by the positioning of the pads. Additionally, the step of applying lateral pressure may include providing an elongated flexible band adapted for applying a compressive force to a human limb having a tendon and a pair of spaced-apart pads supported on the band and positioning said pads on the lateral sides of a tendon for applying the compressive force to the tendon when received between the pads.

BRIEF DESCRIPTION OF THE DRAWINGS

For the purposes of illustrating the invention, there is shown in the accompanied drawings a strap assembly in accordance with one embodiment form of the present invention in various applications.

DETAILED DESCRIPTION

Figure 1A:
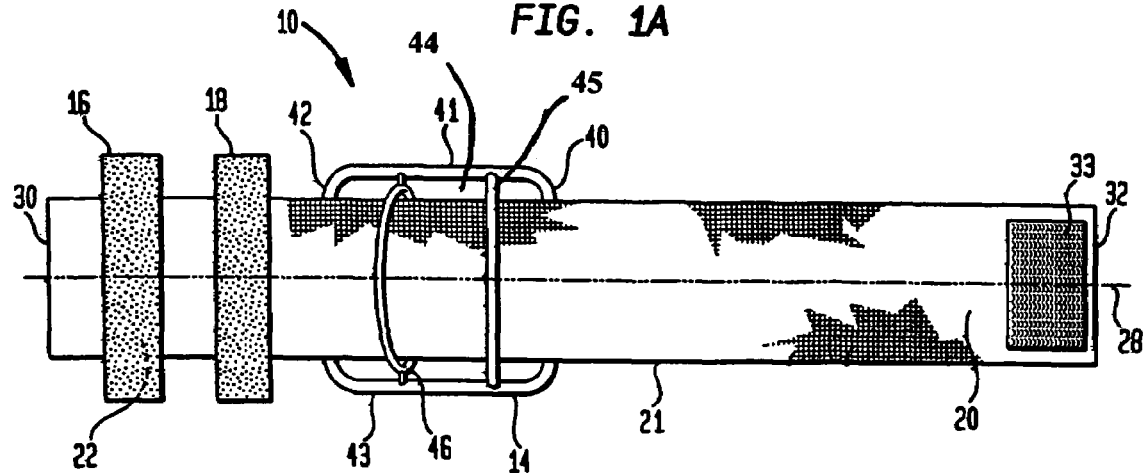
FIG. 1A is a top view of one embodiment of a strap assembly.

Referring now to the drawings, a strap assembly is illustrated in FIG. 1A generally designated by reference 10. The strap 10 preferably includes an elongate flexible band 12, a fastener 14, first pad 16 and second pad 18. Although the band 12 may be formed from any suitable flexible material, the band 12 is preferably formed of a narrow band of elasticized woven or knitted material.

Figure 1B:
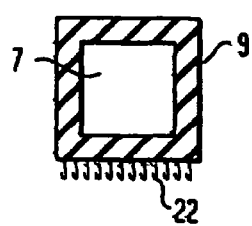
FIG. 1B is a cross-sectional view of one embodiment of a pad.

As illustrated in FIG. 1B, pads 16 and 18 preferably include a base 7. The base 7 may be formed using foam, gel, an air bladder, cloth or the like. A cloth covering 9 may be placed about the base. Pads 16 and 18, more specifically cloth covering 9, may be integrally woven with band 12 or attached to band 12 using various other techniques. In a preferred embodiment, pads 16 and 18 are removably attached to band 12. The pads are disposed along an interior surface 20 of band 12. In one such embodiment, pads 16 and 18 may either include a plurality of hooks or loops 22, i.e., Velcro®, disposed on their entire surface or at least a portion thereof. Band 12 may correspondingly include Velcro® disposed along its interior surface 20. This configuration enables first pad 16 and second pad 18 to be releasably attached along the interior surface of band 12.

Fastener 14 preferably includes four bars, 40, 41, 42 and 43 forming a substantially rectangular shape. Bars 40 and 42 are remote from one another and extend perpendicular to longitudinal axis 28. Bars 41 and 43 extend substantially parallel to a longitudinal axis 28 and connect bars 40 and 42 creating a gap 44 therebetween. Fastener 14 preferably also includes bar 45 and loop 46. Both bar 45 and loop 46 extend between bars 41 and 43 and are remote from bars 40 and 42. Fastener 14 may be disposed along longitudinal axis 28 of band 12, tightly grasping the band therein. This is accomplished by placing second end 32 of band 12 through fastener 14. Second end 32 may be intertwined below bar 42 through loop 46, above bar 45 and then below bar 40. Second end 32 may then be pulled past fastener 14 until the fastener is correctly positioned around band 12. In order to retain a human limb within the strap assembly 10, second end 32 of band 12 may be brought into proximity of first end 30 of band 12. This creates a closed loop structure for receiving human limbs and the like. Second end 32 may now be partially placed within fastener 14. Specifically, the second end is placed above or below bar 42 and through loop 46. However, once exiting the loop, second end 32 may be folded back on itself to tighten the strap assembly.

Second end 32 may additionally have a plurality of hooks or loops 33, i.e., Velcro®, disposed along its surface for communicating with Velcro® on exterior surface 21 of band 12 to prevent second end 32 from becoming loose. Thus, if the second end is going to be folded back onto itself, after being placed through fastener 14, the Velcro® may be placed on the exterior surface 21 of second end 32. When second end 32 is placed through fastener 14 and then looped back upon itself, it may be secured in place by the interaction between the Velcro®. There are a variety of fasteners 14 that can be used for this purpose such as, for example, a common belt buckle at the first end and holes in the tongue at the second end which are engageable with a prong or wire in a conventional belt buckle; two parts snap connections, with one part being disposed on the tongue of the second end and the second part being disposed along the surface of the strap, although Velcro® fasteners are preferred. Additionally, fastener 14 may also be comprised of simple D-rings as well as more complicated structures.

Figure 2:
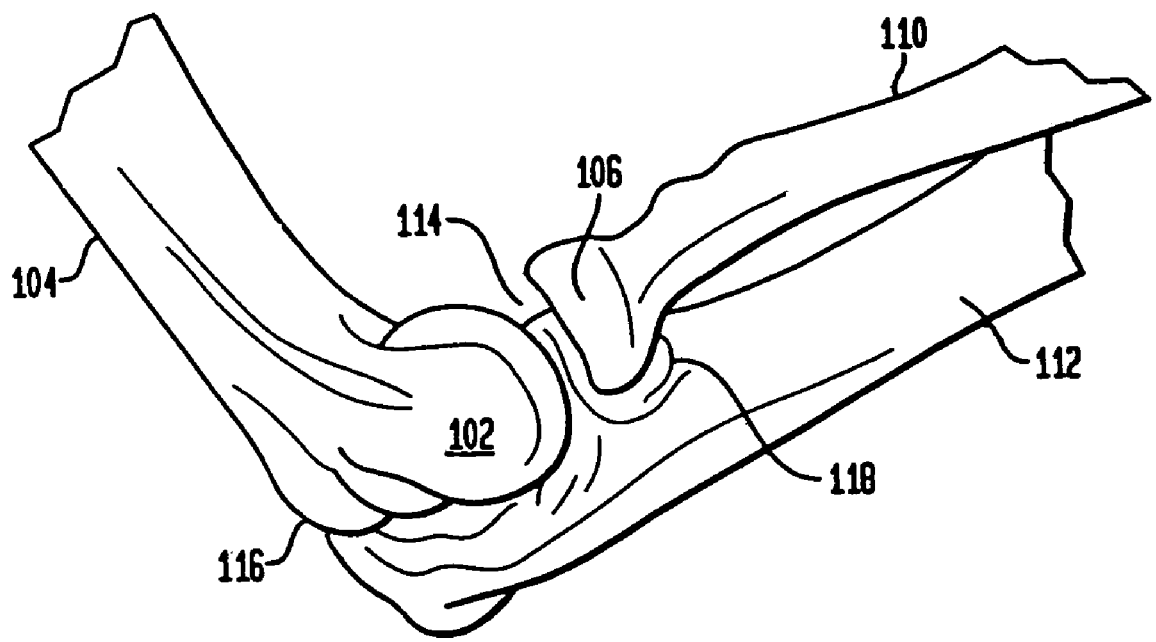
FIG. 2 is a perspective view of the bones and joints of the right elbow of a human during flexion of the elbow.
Figure 3A:
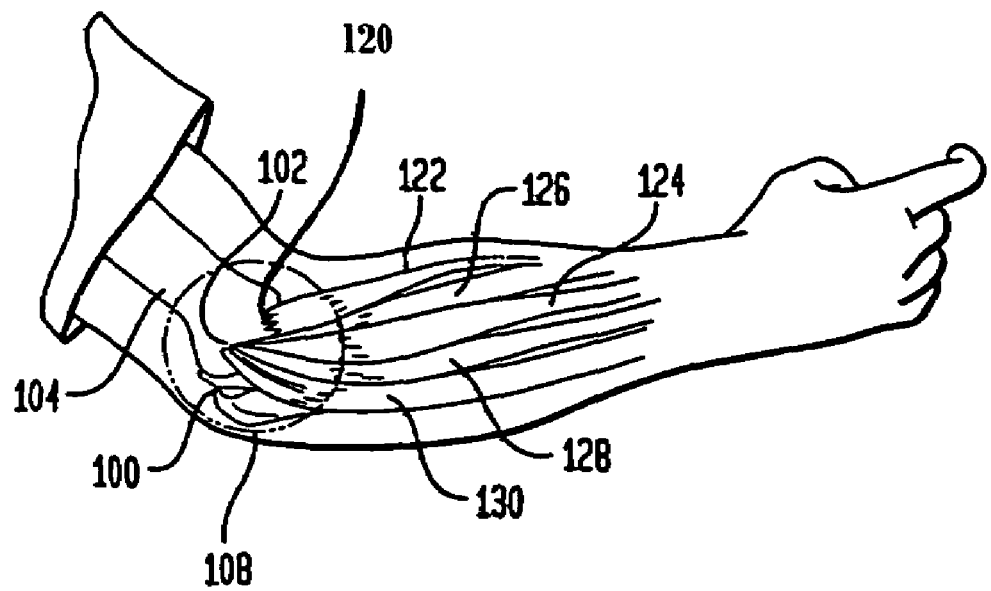
FIG. 3A is a cut-away perspective view of the right elbow and forearm of a human showing the muscles and tendons connected thereto and infected by lateral epicondylitis.
Figure 3B:
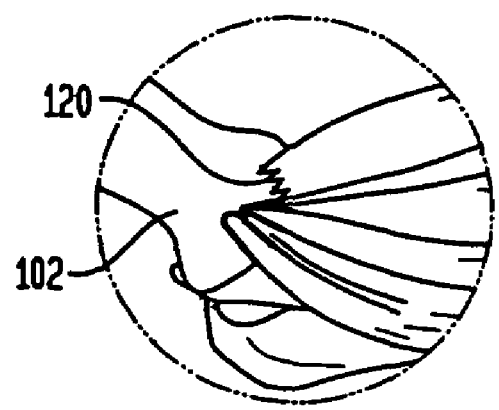
FIG. 3B is a cut-away perspective view of the elbow shown in FIG. 3A illustrating the inflamed tendons and muscles affected by lateral epicondylitis.

Referring now to FIGS. 2, 3A and 3B, the anatomy affected by lateral epicondylitis is shown. FIG. 2 shows the underlying bone and joint structure of a right elbow of a human during flexion. The elbow is formed by the junction of the capitulum 100, medial epicondyle (not shown) and lateral epicondyle 102 of the humerus 104 with the head 106 and olecranon 108 of the radius 110, ulna 112, respectively. The points of which the radius 110, ulna 112 and humerus 104 meet form three joints: the radio-humeral joint 114, the humero-ulna joint 116 and the radio-ulna joint 118. As shown in FIG. 3A, lateral epicondylitis arises from the degeneration and tearing of the superficial muscles along the common tendon attachment 120 where the muscles originate at the lateral epicondyle 102. These muscles include the extensor carpi radialis longus 122, the extensor digitorium 124, the extensor carpi radialis brevis 126, the extensor digitorium 128 and the extensor carpi ulnaris 130. The supinator longus and brevis (not shown) which also originate at the lateral epicondyle, are likewise vulnerable to the degeneration and tearing associated with lateral epicondylitis.

FIG. 3B shows a detailed view of the tearing which occurs when the common tendon attachment 120 results in lateral epicondylitis. Without proper diagnosis and treatment, the pain initially felt by the stressed and torn tendons may be exacerbated. Such complications may be avoided by early diagnosis and treatment which incorporates strap assembly 10 of the present invention.

Figure 4:
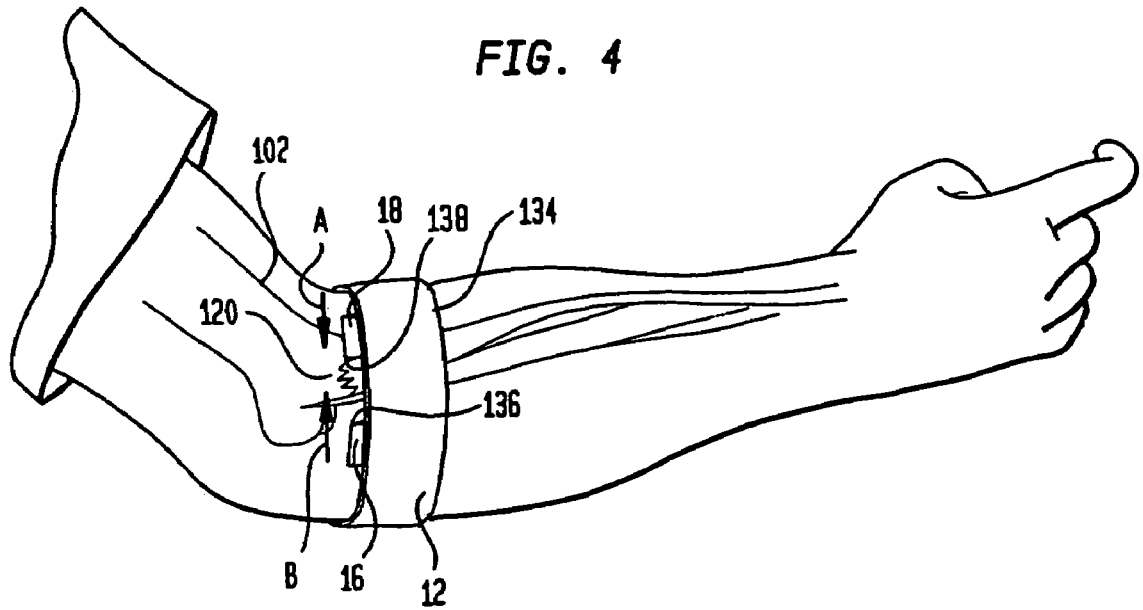
FIG. 4 is a cut-away perspective view of the right elbow and forearm illustrating placement of the strap assembly about the forearm adjacent a tendon for lateral epicondylitis.

Referring now to FIG. 4, the manner in which strap assembly 10 is attached to the right elbow of a human is disclosed. FIG. 4 highlights an irritated tendon 120 subjected to micro-trauma/inflammation tearing caused by overuse. In order to alleviate the discomfort associated with this affliction, pads 16 and 18 may be disposed against the skin of the arm on adjacent sides of tendon 120. The pads create gap 134 positioned between the two. The skin overlying the tendon and more importantly the tendon, must be sufficiently placed within gap 134. In other words, the tendon is preferably placed deep within gap 134 so that edges 136 and 138 of pads 16 and 18, respectively, are positioned adjacent and both lateral and medial to the tendon. The rest of strap assembly 10 is then configured about the forearm with the band 12 circumferentially surrounding the forearm.

Although not shown in FIG. 4, band 12 may be tightened using fastener 14 in order to increase the pressure applied against the arm. While the strap assembly 10 is tightened, edges 136 and 138 overlying the skin apply a lateral force against the tendon in a direction indicated by arrows A and B illustrated in the drawing. The lateral force pinches by compression the tendon and absorbs pressure exerted by the arm on the tendon. The resultant lateral forces differ from prior art assemblies which place direct pressure against a tendon, forcing the tendon to be compressed against underlying tissue or a bone such as the lateral epicondyle 102.

Figure 5:
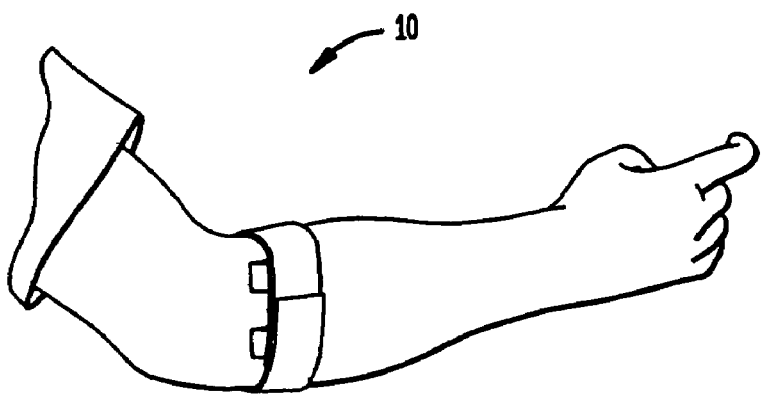
FIG. 5 is a perspective view of a strap assembly in use according to one embodiment of the invention.

Band 12 may be tightened or loosened about the forearm to increase or decrease the pressure exerted by pads 16 and 18 against the tendon. In order to tighten band 12, second end 32 is placed within a loop of fastener 14. The second end 32 is pulled through the loop causing the band 12 to further be drawn through the loop. This movement reduces the closed loop created by second end 32 being brought into proximity of first end 30. As the closed loop is reduced, a restrictive force is exerted against the arm placed within the opening. Continued reduction of the opening, increases the circumferential force exerted by band 12 about the arm, as well as the lateral forces exerted by the pads 16, 18 on the tendon. As previously mentioned, once the correct pressure, i.e., loop size, has been determined, the second end 32 may be attached to the exterior surface 21 of band 12 to secure the strap assembly in place. A correctly positioned and placed strap assembly is illustrated in FIG. 5.

The ease and application of the present invention enables not only physicians and therapists to correctly place the strap assembly but users of all types and ages as well. Strap assembly 10 may be employed while conducting physical activity to decrease the risk of further injury by absorbing some of the forces exerted on a tendon. Additionally, strap assembly 10 may also be utilized to alleviate some of the pain felt and realized after prolonged activity.

The present invention may also be adapted to treat other forms of tendonitis such as, but not limited to "Golfer's Elbow", and the like.

Figure 6:
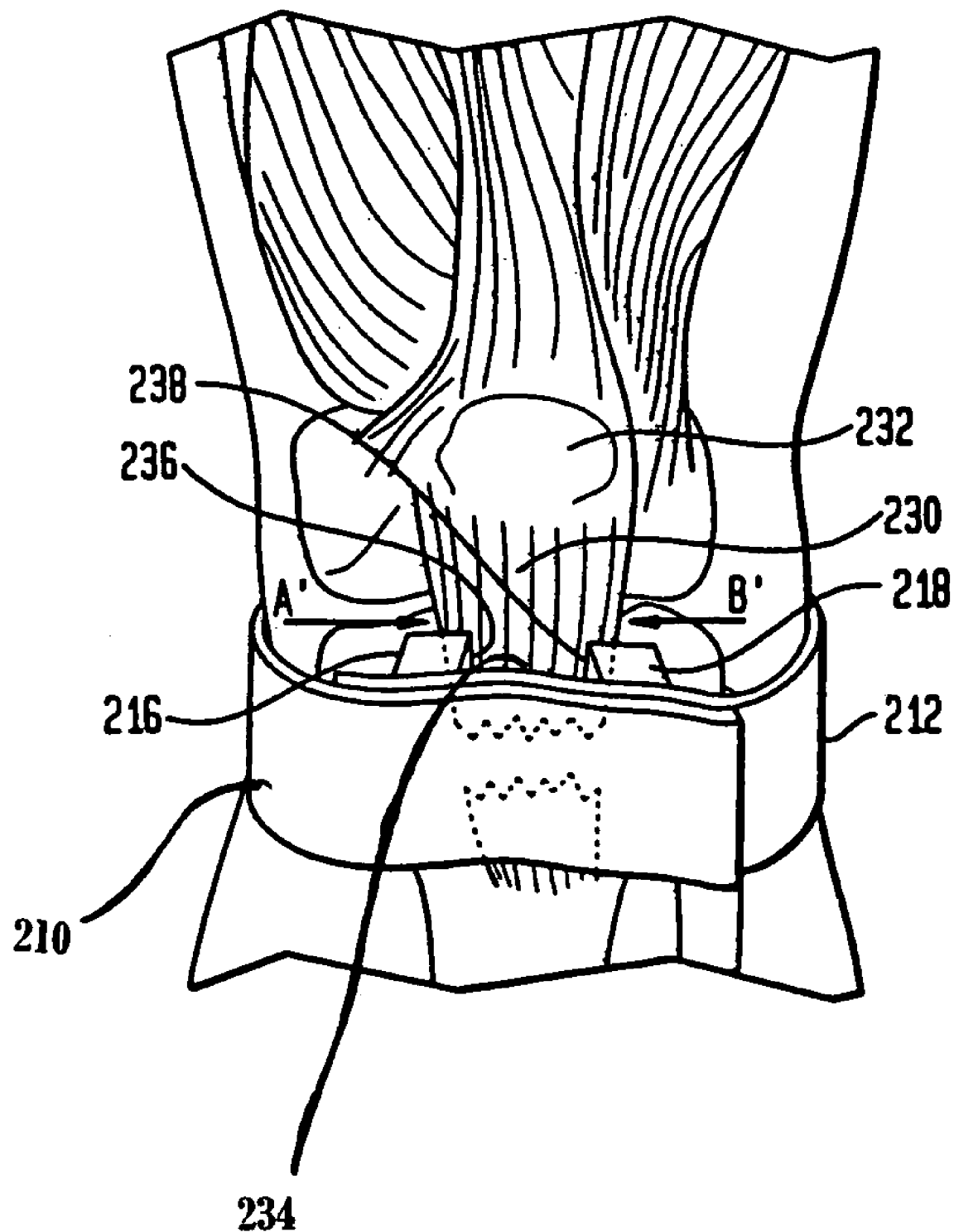
FIG. 6 is a cut-away perspective view of a knee illustrating various muscles and tendons as well as the strap assembly positioned about an injured tendon.

The present invention may also be employed to treat pain associated with tendinitis of the knee. One common form of pain which occurs in the knee is patellar tendinitis also known as "jumper's knee". Jumper's knee is a result of knee degeneration and micro-tearing/inflammation of the patellar tendon 230 along its point of attachment to the inferior pole of the patella 232 as illustrated in FIG. 6. Although many forms of tendinitis may occur in the knee, the present invention will be detailed with reference to "jumper's knee" although strap assembly 10 may be utilized to alleviate pain associated with many forms of tendinitis.

Similar to the application of strap assembly 10 with regard to the forearm, strap assembly 210 may be positioned about the circumference of the knee. First and second pads 216 and 218 are first placed against the skin of the knee adjacent to the tear in the tendon. As with the previous embodiment, pads 216 and 218 are separated by a distance to form a gap 234. The tendon must be placed within gap 234 to allow edges 236 and 238 of pads 216, 218, respectively, to abut the sides of the tendon. The strap assembly 210 may then be tightened so that pads 216 and 218 exert a lateral compressive force against the tendon as indicated by arrows A' and B' in the figure. The skin underlying the pads should be slightly pinched in order that the patellar tendon may be placed correctly within the gap 234 between the pads 216 and 218.

In an alternate embodiment, not shown, the strap assembly may include a cutout. In such an embodiment, the cut out is positioned posteriorly. This is particularly advantageous when the strap assembly is used on the knee, and helps to prevent occlusion of the popliteal artery or compression in the popliteal space. This may also eliminate compression of the fibular head.

Strap assembly 210 may be placed against the inflamed area during activity to relieve pressure exerted on a tendon. Additionally, the strap may be utilized to alleviate pain and discomfort experienced due to the tearing in a tendon.

Figure 7A:
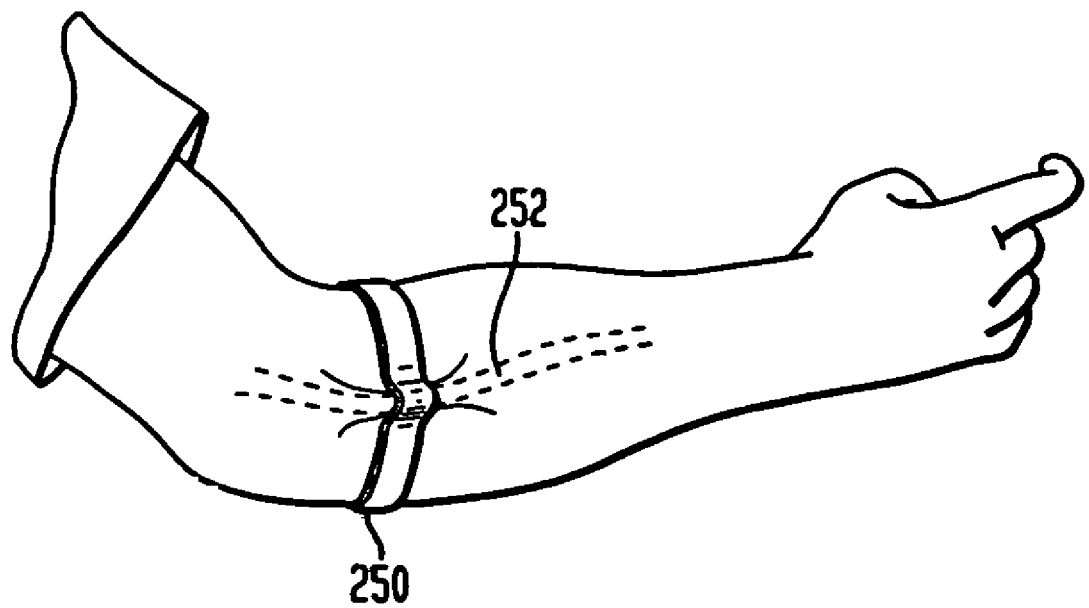
FIG. 7A is a perspective view of one embodiment of the present invention.
Figure 7B:
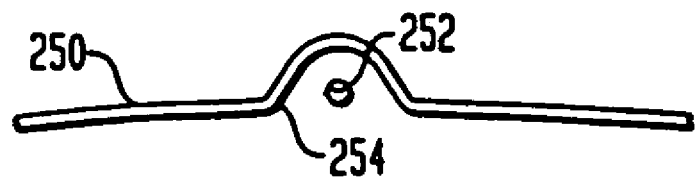
FIG. 7B is a cross-sectional view of the embodiment of FIG. 7A.

In an alternate embodiment, a band or simply a piece of tape 250 maybe utilized to carryout the present invention. As shown in FIGS. 7A and 7B, the skin overlying tendon 252, and tendon 252 is pinched with a lateral pressure possibly by hand. This results in a slight bump 254 created on the limb. The tape 250 is than positioned on the down slopes of the bump, carefully maintaining the lateral pressure. Two pieces of the tape mare anchored about the tissue adjacent to the irritated tendon. The anchored tape is pulled in an approaching fashion creating lateral pressure. The free ends of the two-piece tape are attached to one another then fastened to the limb. The tape may then be wrapped around the limb and secured in place. With the tendon slightly positioned higher than the surrounding tissue, the restrictiveness of the taping can maintain the lateral pressure against the tendon.

Figure 8:
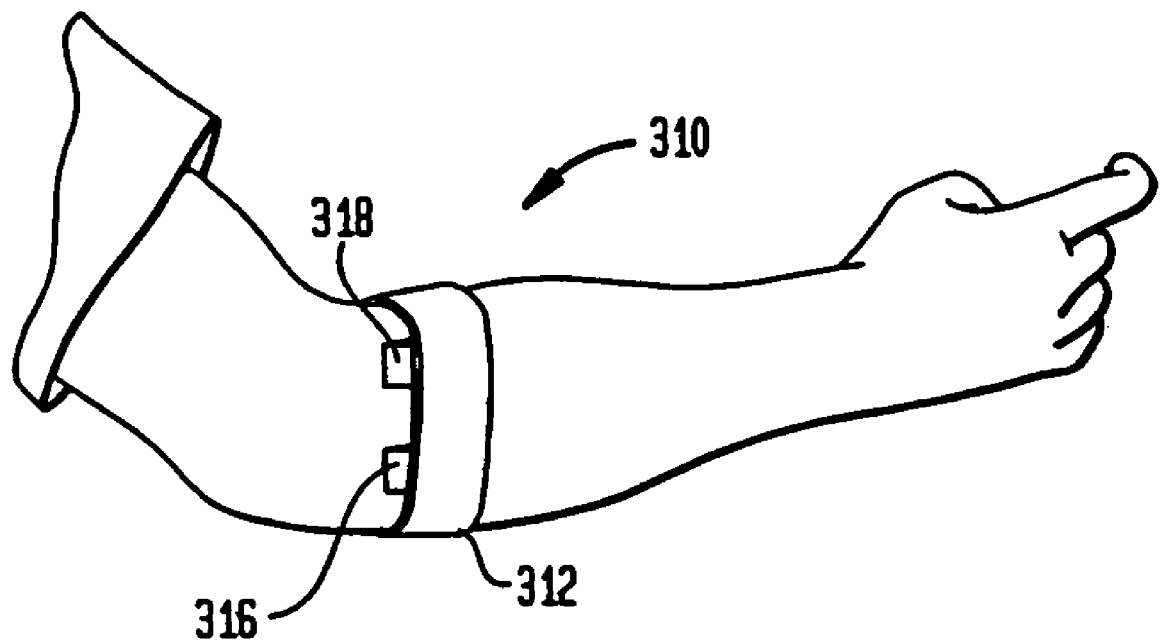
FIG. 8 is a perspective view of one embodiment of the present invention.

In an alternate embodiment as shown in FIG. 8, strap assembly 310 may include band 312 and pads 316, 318. Band 312 differs from band 12 in that band 312 does not include an end and essentially has a closed loop construction. Band 312 may be slid up a human limb and be positioned, for example, about the forearm. Once pads 316 and 318 have been placed correctly adjacent a tendon, band 312 may be slid over the pads to apply a circumferential force against the forearm. The circumferential force causes pads 316, 318 to apply a lateral force against the tendon. Band 312 may come in different sizes so as to apply the correct pressure and force for an individual user.

Figure 9A:
FIGS. 9A and 9B illustrate an additional embodiment of the present invention.
Figure 9B:
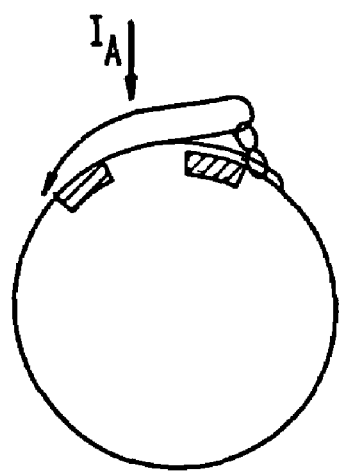
Figure 10A:
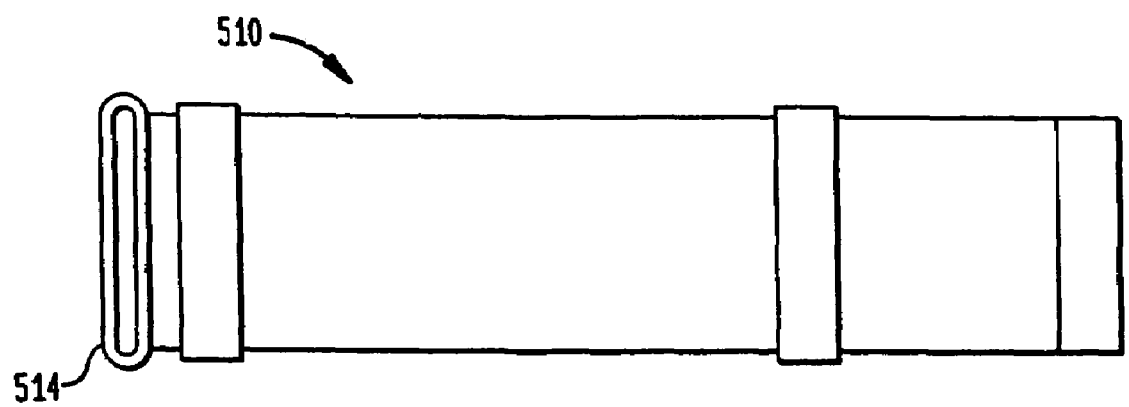
FIGS. 10A, 10B and 10C illustrate an additional embodiment of the present invention.
Figure 10B:
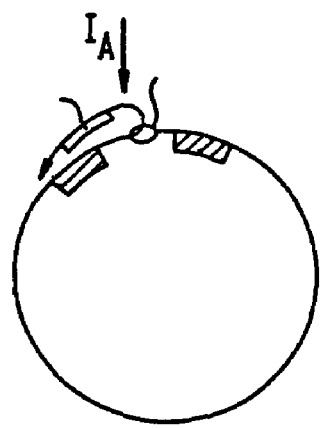
Figure 10C:

FIGS. 9A and 9B and FIGS. 10A and 10B illustrate two additional embodiments of the present invention. Specifically, in FIGS. 9A and 9B, strap assembly 410 may include band 460 attached to band 412. Band 460 is adapted for looping through fastener 414 in order to help the assembly form a closed loop as shown in FIG. 9B. Similarly FIGS. 10A-10C illustrate an alternate locking system with fastener 514 being disposed at one end of strap assembly 510.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating discomfort associated with a tendon, the method comprising applying direct lateral pressure to the lateral sides of a tendon wherein said step of applying lateral pressure includes an elongated strap around the limb bearing against the tendon and at least two pads between the strap and the limb so that the strap holds the pads against the lateral sides of a tendon, positioning said pads against a human limb on opposite sides of the tendon, and tightening said band to cause said pads to apply said lateral pressure to said tendon.

2. The method of treating discomfort associated with a tendon according to claim 1, wherein said tendon is a tendon originating from the medial or lateral epicondyle tendon.

3. The method of treating discomfort associated with a tendon according to claim 1, wherein said tendon is a patellar tendon.

4. The method of treating discomfort associated with a tendon according to claim 1, further comprising adjusting said fastener for controlling said lateral pressure.

5. The method of treating discomfort associated with a tendon according to claim 1, wherein the step of applying lateral pressure includes pinching a portion of skin overlying the tendon in order that the tendon is drawn within a gap formed by the positioning of said pads.

6. The method of treating discomfort associated with the tendon according to claim 1, further comprising means for applying a compressive force to a human limb having a tendon.

7. A method of treating discomfort associated with a tendon, the method comprising applying direct lateral pressure to the lateral sides of a tendon, wherein the step of applying lateral pressure includes providing an elongated flexible band adapted for applying a compressive force to a human limb having a tendon, and a pair of spaced-apart pads supported on said band and positioning said pads on the lateral sides of said tendon for applying said compressive force to the tendon when received between said pads.

8. A method of treating discomfort associated with a tendon, the method comprising applying pressure to the tendon perpendicular to the direction of the fiber orientation of the tendon wherein the pressure is applied by a first pad proximate a first side of the tendon and a second pad proximate a second side of the tendon.

9. The method according to claim 8, wherein the pressure is applied to opposite sides of the tendon, the sides being remote from one another.

10. The method according to claim 8, wherein the tendon is a tendon originating from the medial or lateral epicondyle tendon.

11. The method according to claim 8, wherein the tendon is a patellar tendon.

* * * * *